United States Patent [19]

Little et al.

[11] Patent Number: 5,108,710
[45] Date of Patent: Apr. 28, 1992

[54] TRANSDERMAL PATCH HOLDER

[76] Inventors: Amy C. Little, 643 Collier Rd., Atlanta, Ga. 30318; James E. Swon, 12 Twin Park Dr., Brookside, N.J. 07926

[21] Appl. No.: 617,560

[22] Filed: Nov. 26, 1990

[51] Int. Cl.$^5$ .............................................. A61F 13/56
[52] U.S. Cl. .................................... 422/104; 435/310; 604/304; 604/307; 604/308
[58] Field of Search ............................ 422/104, 99, 58; 435/310; 128/157; 604/289, 304, 307, 308

[56] References Cited

U.S. PATENT DOCUMENTS

| | | | |
|---|---|---|---|
| 3,212,495 | 10/1965 | Osbourn et al. | 604/307 X |
| 4,668,472 | 5/1987 | Sakamoto et al. | 422/104 X |
| 4,743,249 | 5/1988 | Loveland | 604/307 X |
| 4,988,341 | 1/1991 | Columbus et al. | 604/304 X |

*Primary Examiner*—Lynn Kummert
*Attorney, Agent, or Firm*—William T. Hough

[57] ABSTRACT

In a preferred embodiment of the invention, a transdermal patch holder is provided for making possible an ascertaining of drug release rate of a transdermal patch mountable thereon. The holder includes upper and lower spaced-apart aligned annular adapter disc structures forming aligned through-spaces. An upper surface of the lower disc structure has a centrally positioned stepped indentation forming a recess space seatable of the transdermal patch. The lower surface of the upper disc structure has a centrally positioned stepped downwardly-extending projection of slightly lesser cross-section than the cross-section of the recess space and is adapted to downwardly press upon an upper surface of a seated transdermal patch when the upper disc structure is intermittently in a latched state of being latched to the lower disc structure. A latching mechanism provided by outer circumscribing upright edges at each of opposite sides of each of the upper and lower disc structures has spaced-apart cut-aways forming a radially outwardly extending lateral projection therebetween, and lateral projections of the upper and lower disc structures aligned and having elastic annular bands intermittently mounted thereon securable of the upper and lower disc structures in face to face relationship. A transdermal patch is mountable and may be thereby held therebetween, with a handle-tab of the patch being seatable in and extendable through a laterally extending channel to laterally exterior space.

28 Claims, 3 Drawing Sheets

TRANSDERMAL PATCH HOLDER

This invention is directed to a novel transdermal patch holder in which the release rate of drug is ascertainable for profiling in-vitro drug delivery of transdermal patches.

PRIOR ART

Although there have existed heretofore other transdermal patch support structures for testing rate of release of the drug carried thereby, there are no known prior art structures nor patents for structures comparable to the present invention, a novelty patent search having been conducted in United States Patent and Trademark Office Class 604, subclasses 304 and 307, Class 269, subclasses 322 and 909, Class 423, subclass 215.5, Class 73, subclasses 73, 76, and 866, and Class 428, subclass 254, together with consultation with a government examiner. Loveland U.S. Pat. No. 4,743,249 granted May 10, 1988 is directed to the subject matter of dermal and transdermal patches of one general type that can be tested within the holder of the present invention, but the present invention not being limited thereto. In one typical prior transdermal patch-mounting combination, a mesh screen is clipped to a watch glass, with a transdermal patch held therebetween, its mesh screen being undesirably in contact with the upper face-active surface of the drug-containing transdermal patch whereby the mesh screen partially blocks many areas of the upper surface of the transdermal patch to exposure to a leaching liquid, as well as the mesh screen potentially mutilating or altering leaching-properties of the active surface of the transdermal patch. Also in such an arrangement, the watch glass, clips and the transdermal patch sit very high in the testing vessel thereby creating an exceptionally undersirably large amount of dead volume of leaching-solution "below" the unit. This is due to the extended diameter created by the above-noted clips of that apparatus and arrangement. Additionally, imperfect and varying circumferences of standard watchglasses cause each unit to sit or rest differently in the testing vessel, resulting in a lack of standardization and inconsistent results during dissolution test(s). Such apparatus is moreover limited to small patches only. In a different other prior arrangement, a screen having an annular mounting structure, has the transdermal patch intermittently adhered or glued thereto, which experience therewith has resulted in the determination that a glued patch proves difficult to handle, assemble and/or work with under laboratory testing conditions, being less than a sturdy combination. Edges of the adhered or glued patch may or may not leak leachable liquid at the edges thereof or may or may not be securely adhered or glued to a totally anchored state at all points around the annular support to the screen. Also, the diameter of the above-noted apparatus is 3.5 cm, making it unusable for patches that are of larger area. In still another embodiment, a patch is glued to a curved revolvable surface for revolving the patch within leachable liquid. In such arrangement, not only is the glue not reliable nor dependable for unqualified assurance of total anchoring of the transdermal patch, but the reservoir is stressed backwards against the curve of the cylinder, thereby realistically potentially stretching or breaking the membranes and/or seal thereby with a hazard of altering the release pattern to result in inacurrate and faulty and incorrect readings as to release pattern. In another apparatus utilized for ascertaining drug release rate for a transdermal patch utilizing a permeable membrane over an opening to a reservoir containing drug(s), there is provided a cell described in French Pharmacopoeia, with the cell consisting of an annular reservoir having a plurality of upwardly-extending spaced-apart bolts having upper threaded distal ends and having the heads thereof embodied (embedded) in (within) the reservoir, and an annular lid having vertical through-holes alignable with and receivable of the upper distal ends of the space-apart bolts, and additionally there are nut-like female-threaded members mountable on the upper distal ends of the bolts whenever the lid is bolted thereon, subsequent to inserting the drug-containing receptacle and its membrane to a position seated within a defined hole of the annular reservoir.

BACKGROUND TO THE INVENTION

Dermal and transdermal systems and the technology thereof are conventionally well known and include therapeutic devices that have been designed to be applied on and held by typically an adhesive band directly to and in contact with the skin in desired or needed places or areas of typically the human body. Each patch of such systems holds or is the vector for holding one or more drugs that is/are designed to exert an action after release onto the skin and/or penetration through the skin covered by such patch(es). Typically composition or preparation applied to or embodied in a transdermal patch is composed of liquid, semi-solid or solid preparation in which drug(s) is/are dispersed, embodied and/or dissolved at a defined predetermined concentration, usually being in a high concentration. The patch(es) or membrane(s) is/are designed (engineered) to release drug according to a defined rate pattern—conventionally referred to as release rate. Alternately, a device such as the above-described cell type patch holder, typically includes a drug-containable patch-reservoir (container) having drug(s) placed therein and covered (restrained therein) by a particular especially selected or prepared membrane characterized with predetermined permeability to passage of the drug(s) when placed in contact with the skin. In any of such typical types of transdermal patches, the profile of release rate of the drug(s) must be determined accurately and reliably by use of a transdermal patch holder by which the patch may be subjected to drug relase by a leachable liquid. Use of the above-described nut and bolt type cell has proven to be cumbersome in use, as well as excessively time consuming in the matching of the bolt-receivable holes with the bolts, and thereafter screwing-on typically four separate nuts of four separate bolts. Another problem with the above-described nut-bolt cell arises from the annular reservoir being susceptable to failure to seat stably and securely the mounting edges of a reservoir-membrane type patch, which could lead to erroneous, faulty and/or inconsistent results in the leaching of the drug. Another problem arising from this particular prior art arrangement, is that the height of the unit results in the patch utilized sitting deeply in the holder thereby preventing maximum exposures to the movement of the leaching liquid or solution.

Prior to the present invention, in the technology of profiling of transdermal drug delivery systems represented by different types of transermal patches, there have existed problems associated with securing consistent and reliable determinations of release rate(s)

thereof, such as above-described problems in the preceding paragraph. Additionally heretofore, mechanisms for supporting such transdermal patches have been cumbersome and bulky, requiring additional preparations such as adhesives and most importantly not having been standardized in regard to circumference and/or positioning within the leaching-vessel, for example. Another problem present has been the difficulty heretofore to unhindered exposure of drug-containing reservoirs to a body of leaching liquid. The art of measuring the amount of drug released in various types of leaching liquids for different types of drugs, is well known conventional prior art, and is not the subject matter of this invention. However, proper exposure of active surfaces and/or standardization of the holders are very important to properly ascertain reliably the true in-vitro rate of drug-release, and heretofore the prior apparatuses have not been optimal.

OBJECTS OF THE INVENTION

Objects of the invention include obtaining a transdermal patch holder that overcomes and/or avoids problems and/or difficulties and disadvantages of the types above-noted, together with obtaining other novel benefits and advantages.

More particularly, a primary object is to provide a transdermal patch holder that consistently exposes the same drug-containing patch area evenly across the surface of the patch to leaching liquid to a consistent and evenly distributed degree of exposure across the entire surface of the drug-containing portion of the patch, whereby accurate and repeatable profiling results of a particular transdermal patch's release rate is reliably ascertainable.

Another particular object is to provide a transdermal patch holder that securely holds a transdermal patch in a predetermined fixed and stable position that is repeatable by future follow-up tests of comparable transdermal patches, whereby degree of exposure to an ascertainable amount of leaching liquid may be determined and/or held constant in repeated test trials of comparable patches in the profiling of the transdermal drug delivery system of that particular type transdermal patch.

Another object is to provide a transdermal patch holder achieving one or more prior objects, together with achieving maximum exposure to an ascertainable amount of leaching liquid to a controlled extent such that profiling results are consistently and reliably repeatable for a particular type of transdermal patch holder for its specifically contained drug held thereby.

Another object is to obtain a transdermal patch holder that achieves maximum exposure of a transdermal patch contained drug to evenly distributed exposure and leaching possibilities from a leaching liquid, to obtain maximum leaching during the shortest period of time for reliable and repeatable results for a particular type of transdermal patch in the profiling of its delivery system.

Another object more particularly is to provide a transdermal patch holder that has a precision-cut circumference thereby making possible repeatable and sturdy and easily-achievable stably seating thereof with a test tube-shaped vessel, to thereby provide standardization from vessel to vessel, and/or to minimize dead volume in the bottom of a vessel in which leaching and drug-release is/are taking place.

Another major object of this invention is to obtain a novel transdermal patch holder characterized by making possible extreme ease and speed in the mounting of transdermal patch(es) suitably for accurate and reliable and repeatable results in the profiling of release rate of drug(s) from mounted transdermal patch(es).

Another object more particularly is to obtain a transdermal patch holder that provides for handling a transdermal patch by its laterally-extending handle while positioning within and locking the transdermal patch holder into its predetermined intermittently locked state and position prior to testing the patch for its drug release rate in the profiling of the transdermal drug delivery system thereof.

Another object is to provide optional embodiments of the present inventive transdermal patch holder such that users thereof have greater flexibility in choosing and selecting the embodiment most suitable for the particular type of transdermal patch to be tested for its drug release rate in the profiling of the transdermal drug delivery system thereof.

Another object is to provide both broad and preferred ranges of dimensions of alternate embodiments of the present invention, found to best achieve other objects of this invention.

Another object is to obtain a transdermal patch holder that may optionally be inverted and/or in which a transdermal patch may be optionally inverted when mounted therein, without altering the seating and securing capability, while retaining secure and firm fitting of the transdermal patch by the transdermal patch holder.

Other objects become apparent from the preceding and following disclosure.

SUMMARY OF THE INVENTION

As above-noted, the transdermal patch holder of this invention is designed to hold a transdermal patch, and in a conventional well known manner the transdermal patch holder is placed in typically a large test-tube type vessel of typically three of four inches diameter and having typically an inner bottom that is concave in the nature of a hemisphere, any conventional liquid such as water being used therein submerging the transdermal patch and inventive transdermal patch holder sufficiently for any conventional stirring device such as revolving blades and/or moving paddles being driven therein to insure continuous and/or continued circulation of the leaching liquid around and about the transdermal patch holder typically resting and supported on the above-described rounded concave bottom of a test-tube type vessel of appropriate size typically as previously described, typically being a one liter beaker having an inner concave hemispherical bottom.

In a broad statement of the invention, there is provided a transdermal patch holder that makes possible an improved more consistent and reliable ascertaining of release rate of drug carried by a transdermal patch, during the profiling of transdermal drug delivery system of one or more of particular transdermal patches carrying predetermined drug(s) in predetermined amount. Broadly, the transdermal patch holder includes a novel combination of novel elements novelly positioned as follows. There are aligned separate upper and lower adapter disc structures. Each of the upper and lower adapter disc structures has opposite upper and lower surfaces. At least one of the upper and lower disc structures has a first through-space of predetermined major first cross-sectional area extending between the upper and lower surfaces thereof. The lower surface of the upper disc structure has at-least some first outer portions thereof and the upper surface of the lower disc structure has at-least some second outer portions. The first outer portions and the second outer portions are in contact or contactable with one-another before and/or after mounting of a transdermal patch therebetween. At least one of the upper surface of the lower disc structure and the lower surface of the upper disc structure has a first stepped indentation of a first predetermined depth forming a first recess space. The first stepped indentation and its first recess space thereof is of a shape and position such that outer edges of a transdermal patch are receivable and seatable of a transdermal patch having a second predetermined cross-sectional area which is greater than the first cross-sectional area of the first through-space. This indentation provides for secure and stable seating of the outer edges of a transdermal patch within the recess formed by the first stepped indentation. Additionally as a novel element in the novel combination, there is/are latching structure(s) and mechanisms thereof providing for intermittently latching-together the above-described upper and lower adapter disc structures whereby a transdermal patch seated or seatable within the recess space is intermittently securely held or adapted to be held in a supported state and position adapted for exposure to leaching liquid in contact with the transdermal patch through the first through-space by which drug is leachable from the transdermal patch.

In a first preferred embodiment, there is included substantially flattened through-channel structures as part of the recess space-containing disc structure. The through-space structure forms a through-channel space at at-least one of opposite sides of and in flow communication with the above-described recess space, and the through-channel space extends laterally to sideward exterior space. The through-space structure is adapted to receive, mount and seat a radially-extending handle-tab of a transdermal patch when a transdermal patch is seated between the upper surface of the lower disc structure and the lower surface of the upper disc structure.

In a second preferred embodiment as a modification and/or variation to the above-described first embodiment, each of the adapter disc structures has a substantially circular upright outer edge circumscribing and positioned between the upper and lower surfaces thereof. In this embodiment, the first stepped indentation is of substantially circular shape thereby providing for improved seating and sealing and sturdiness of the mounting of typically circularly shaped transdermal patch(es).

In a third preferred embodiment as a modification and/or variation to the above-described second embodiment, a remaining one of the lower surface of the upper disc structure and the upper surface of the lower disc structure has a stepped projection of increased disc structure-thickness of a predetermined thickness. In this embodiment, the stepped projection has a substantially circular shape of third predetermined cross-sectional area less in area than the above-described second cross-sectional area such that the stepped projection is seatable within the first stepped indentation; as a result thereof, the stepped projection is pressable on one surface of a transdermal patch sufficiently to restrain the transdermal patch when the transdermal patch is seated within the above-described stepped indentation and its recess thereof, thereby the downwardly pressing projections ascertaining that the transdermal patch is firmly and securely seated in fulfillment of one or more prior recited objects.

In a fourth preferred embodiment as a modification and/or variation on the broad invention, there are the preferred structures and features above-described for the above-described third embodiment.

In a fifth preferred embodiment, as a modification and/or variation on the above-noted fourth preferred embodiment, a remaining one of the aligned upper and lower adapter disc structures also has a second through-space of predetermined major fourth cross-sectional area extending between the upper and lower surfaces thereof whereby each of opposite sides of a transdermal patch supported between the upper and lower aligned adapter disc structures is exposable to surrounding leaching liquid for the leaching of drug therefrom. The through-space within the second (remaining one) of the aligned upper and lower adapter disc structures makes it possible to speedily operatively install (insert) the transdermal patch easily and optionally in either the upright or inverted (upside-down) position, since in either position the drug-leachable membrane thereof will be fully exposed to a leaching liquid.

In a sixth preferred embodiment as a modification and/or variation on the fifth preferred embodiment, the aligned upper and lower adapter disc structures are each composed of polytetrafluoroethylene.

In a seventh preferred embodiment as a modification and/or variation on the fifth preferred embodiment, the aligned adapter disc structures are each composed of stainless steel.

In an eighth preferred embodiment as a modification and/or variation on the seventh preferred embodiment, the upper and lower adapter disc structures each have a thickness ranging from about 0.045 inches to about 0.055 inches, which upper and lower range limits have been found critically to constitute the maximum and minimum operational effective limits possible for substantially achieving foregoing objects such as especially making possible the obtaining of repeatable reliable and accurate measurement and ascertaining of actual and/or total amount and/or degree of release of drug during an ascertainable time period from a transdermal patch being held by the transdermal patch holder of this invention.

As a ninth preferred embodiment as a modification and/or variation on the eighth preferred embodiment, it has likewise been found to be critical on the same basis that for most optimal determinations in achieving profiling of transdermal drug delivery system(s) of transdermal patch(es) being held and thereby being made subjectable to leaching testing, the thickness of the upper and lower disc structures each critically rang(es) from about 0.025 inches to about 0.030 inches.

As a tenth preferred embodiment as a modification and/or variation on the previously described broad invention, the first through-space of predetermined major first cross-sectional area is of circular cross-section formed by an inside diameter of the first stepped indentation critically having an inside diameter ranging critically from about 0.125 inches to about 1.75 inches. In this embodiment, the first stepped indentation has an outside diameter ranging critically from about 0.1 inch to about 2.25 inches wherein the inside diameter is selected to be smaller than the outside diameter. Also in this embodiment, the first stepped indentation having a sufficiently large outside diameter as compared to outside diameter of a drug reservoir such that a transdermal patch is supportable across the first throughspace by support structure of the first stepped indentation. The dimensions of this embodiment are likewise critical for the same reasons stated for the ninth embodiment.

In an eleventh preferred embodiment as a modification and/or variation on the tenth preferred embodiment, the inside diameter of the first stepped indentation ranges critically from about 0.75 inches to about 1.5 inches and the outside diameter of the first stepped indentation ranges critically from about 0.85 inches to about 2.0 inches wherein the inside diameter is selected to be smaller than the outside diameter. In this eleventh preferred embodiment, the first stepped indentation has support structure between the stepped indentation inside diameter and the stepped indentation outside diameter ranging critically from about 0.12 inch and 0.38 inch. The dimensions of this embodiment are likewise critical for the same reasons stated for the ninth embodiment.

In a twelfth preferred embodiment as a modification and/or variation on the eleventh preferred embodiment, the upper and lower adapter disc structures each critically have outside diameters ranging critically from about 1.7 inch to about 2.6 inches. Likewise the dimensions of this embodiment are likewise critical for the same reasons stated for the ninth embodiment.

In a thirteenth preferred embodiment as a modification and/or variation on the twelfth preferred embodiment, there are the preferred structures and features above-described for the above-described fifth preferred embodiment.

In a fourteenth preferred embodiment as a modification and/or variation on the thirteenth preferred embodiment, the latching means comprises at-least two opposite edges of the upright outer edge of each of the aligned adapter disc structures. Each of the opposite edges includes a lateral projection. Additionally there are included at-least two elastic annular members each tightly mountable around aligned lateral projections of the upper and lower discs for each of the two opposite edges whereby the upper and lower adapter disc structures are intermittently held together.

In a fifteenth preferred embodiment as a modification and/or variation on the fourteenth preferred embodiment, each lateral projection is formed by spaced-apart cut-outs in the upright outer edge defining (forming) the lateral projection therebetween whereby distal portions of each lateral projection are substantially flush with the above-described upright outer edge.

In a sixteenth preferred embodiment as a modification and/or variation on the thirteenth preferred embodiment, the latching means includes aligned upper and lower support-disc structures with the upper support-disc structure positioned above the upper adapter disc structure. In this sixteenth preferred embodiment, the lower support-disc structure is positioned below the lower adapted disc structure, and the upper and lower adapter structures are aligned with the upper and lower support-disc structures. Also, each of the upper and lower support-disc structures have upper and lower faces, with the upper and lower support-disc structures being intermittently securable in a position having the upper support-disc's lower face pressing downwardly on the upper surface of the upper adapter disc structure and with the lower support-disc having its upper face pressing upwardly on the lower surface of the lower adapter disc structure. In this sixteenth preferred embodiment, at least one of the upper and lower support-disc structures has a centered through-space extending between the upper and lower faces.

In a seventeenth preferred embodiment as a modification and/or variation on the sixteenth preferred embodiment, the lower face of the upper support-disc structure includes a second recess space of third predetermined cross-sectional area. That third predetermined cross-sectional area critically must be sufficiently large to receive and seat the upper disc structure. Also in this seventeenth preferred embodiment, the upper face of the lower support-disc structure includes a third recess space of fourth predetermined cross-sectional area. Likewise, the fourth predetermined cross-sectional area critically must be sufficiently large to receive andd seat the lower disc structure. Criticality of the largness of the third and fourth cross-sectional areas determines operativeness, being obviously inoperative as to this preferred embodiment in the absence of such sufficient largness as above-stated.

In an eighteenth preferred embodiment as a modification and/or variation on the seventeenth preferred embodiment, the latching means includes at-least two opposite support-disc edges of each of the upper and lower support-disc structures. Each of the opposite support-disc edges includes a lateral projection. Additionally in this eighteenth preferred embodiment, there are included at-least two elastic annular members each tightly mountable around each of aligned pairs of the lateral projections of the upper and lower support-disc structures whereby the upper and lower adapter disc structures are adapted to be intermittently held together.

In a nineteenth preferred embodiment as a modification and/or variation on the eighteenth preferred embodiment, each lateral projection is formed by spaced-apart cut-outs in the two opposite support-disc edges to define the lateral projection therebetween whereby each of distal portions of each lateral projection is substantially flush with its upright outer edge of the support-disc structures.

In a twentieth preferred embodiment as a modification and/or variation on the nineteenth preferred embodiment, each of the upper and lower support-disc structures includes the centered above-noted through-space, thereby enabling the upper and lower support-disc structures to be optionally inverted and operational equally well in either state, thereby providing for ease and speed in installing the disc structures and the transdermal disc therebetween, and final mounting thereof and quick and easy insertion thereof into a leaching vessel of stirred leaching liquid.

In a twenty-first preferred embodiment as a modification and/or variation on the twelfth preferred embodiment, the upper and lower adapter disc structures each have outside diameters ranging critically from about 1.0 inch to about 3 inches as a broad range. Likewise the dimensions of this embodiment are likewise critical for the same reasons stated for the ninth embodiment.

In a twenty-second preferred embodiment as a modification and/or variation on the broad invention, there are the preferred structures and features above-described for the above-described sixteenth preferred embodiment.

In a twenty-third preferred embodiment as a modification and/or variation on the twenty-second preferred embodiment, there are the preferred structures and features above-described for the above-described seventeenth preferred embodiment.

In a twenty-fourth preferred embodiment as modification and/or variation of the twenty-third preferred embodiment, there are the preferred structures and features above-described for the above-described fourteenth preferred embodiment.

In a twenty-fifth preferred embodiment as a modification and/or variation of the twenty-fourth preferred embodiment, there are the preferred structures and features above-described for the above-described fifteenth embodiment.

In a twenty-sixth preferred embodiment as a modification and/or variation on the twenty-fifth preferred embodiment, the upper and lower support-disc structures each have outside diameters ranging critically from about 1.0 inch to about 3 inches. Likewise the dimensions of this embodiment are likewise critical for the same reasons stated for the ninth embodiment.

In a twenty-seventh preferred embodiment as a modification and/or variation on the twenty-sixth preferred embodiment, the upper and lower support-disc structures are stainless steel.

In a twenty-eighth preferred embodiment as a modification and/or variation on the twenty-second preferred embodiment, there are the preferred structures and features above-described for the above-described twenty-seventh preferred embodiment.

The invention may be better understood by making reference to the drawings of the following Figures.

THE FIGURES

FIG. 1A' diagrammatically illustrates the same embodiment as FIG. 1A, symbolically illustrating features and dimensions thereof, also shown in exploded view.

FIG. 2A' diagrammatically illustrates the same embodiment as FIG. 2A, symbolically illustrating features and dimensions thereof, also shown in exploded view.

DETAILED DESCRIPTION

In more detailed description of preceding embodiments, common and/or related indicia are utilized for common and/or related features and/or elements in alternate embodiments of the invention and of the transdermal patch(es) utilized therewith, repeating only in some cases to improve clarity and/or understanding of the invention and/or description thereof.

Figures 1A, 1B:
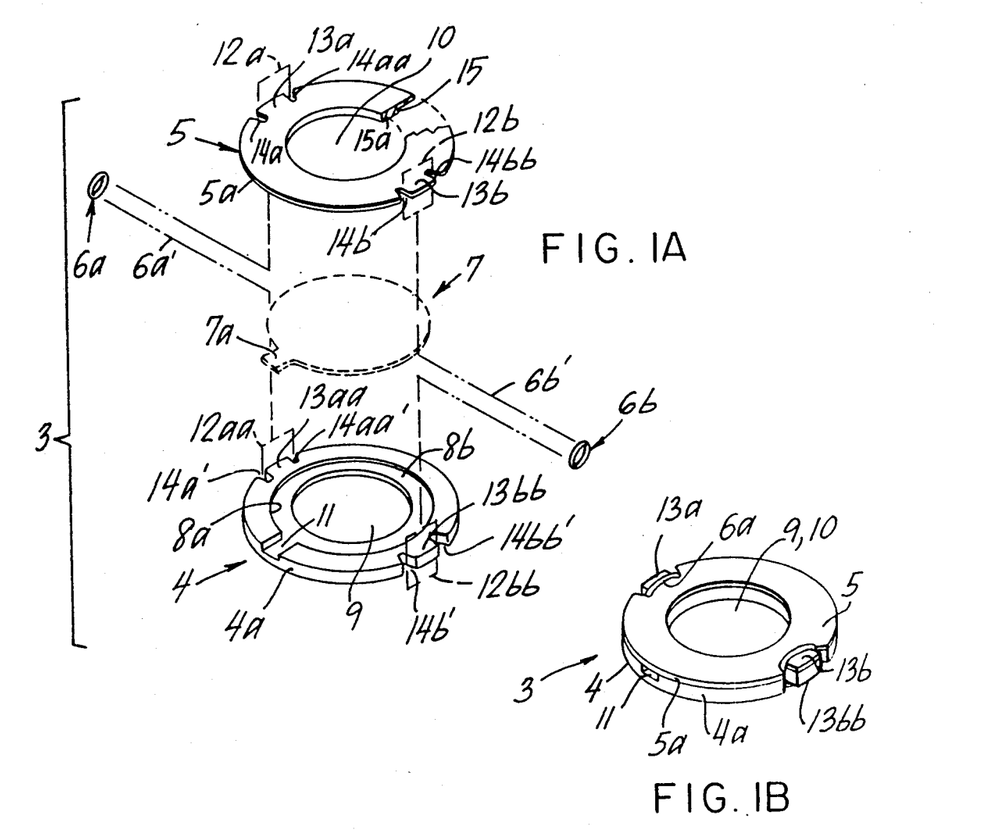
FIG. 1A diagrammatically illustrates a preferred embodiment of the invention shown in top perspective exploded view with partial cut-away, inclusive of a symbolically illustrated typically and properly aligned transdermal patch shown in phantom lines.
FIG. 1B diagrammatically illustrates the same embodiment and features as that of FIG. 1A, except here shown in non-exploded view as it would normally appear, except devoid of a transdermal patch mounted therein.
Figure 1A:
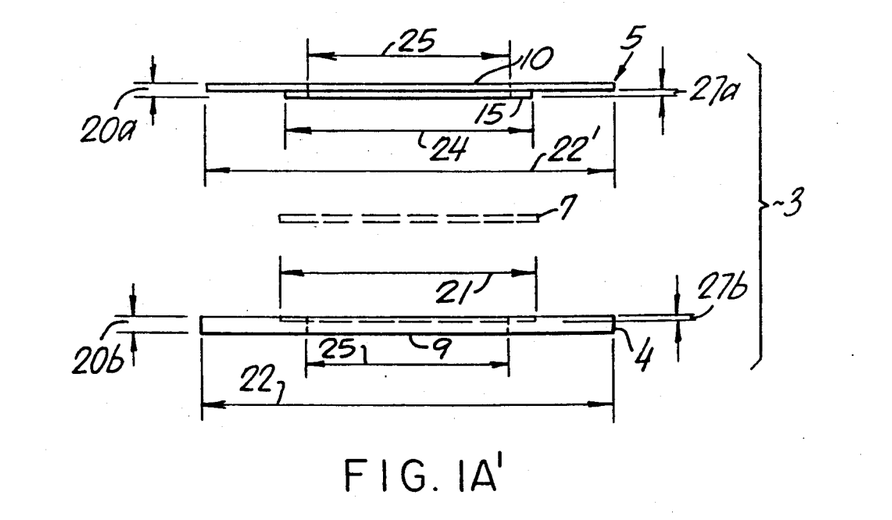
Figure 2A:
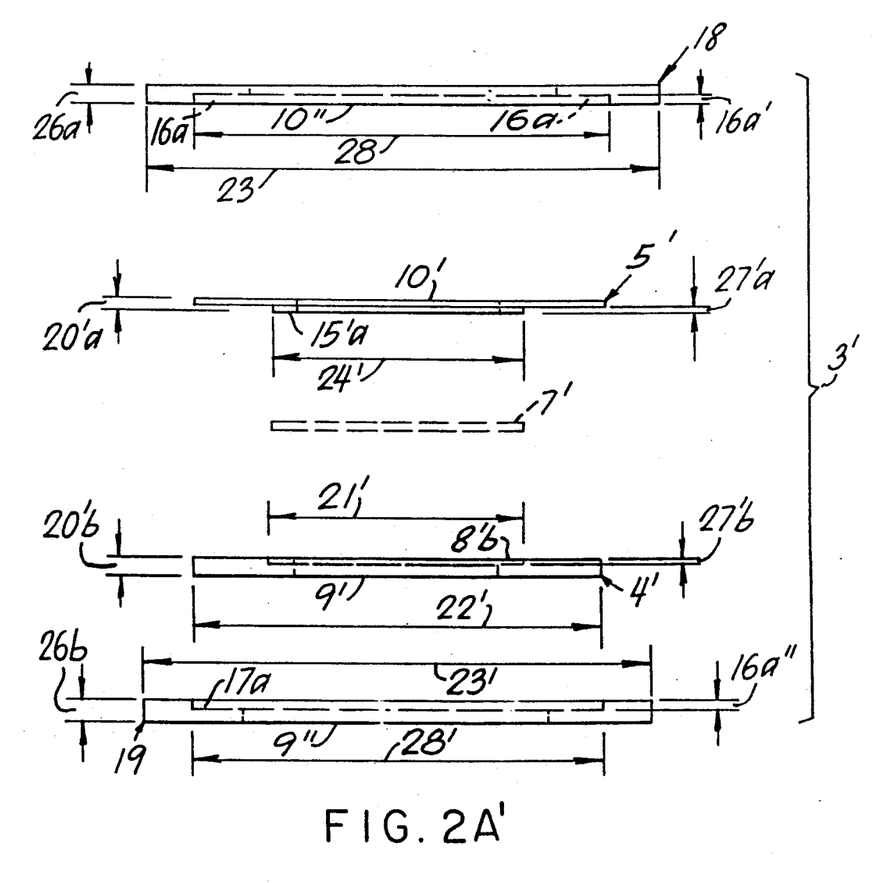
FIG. 2A diagrammatically illustrates another preferred embodiment of the invention also shown in top perspective exploded view with partial cut-away, and also inclusive of a symbolically illustrated typically and properly aligned transdermal patch shown in phantom lines.

With regard to all Figures, for initial clarification and understanding of the invention and the major differences between the embodiment 3 illustrated in FIGS. 1A, 1B and 1A' as compared to embodiment 3' of FIGS. 2A, 2A' and 2B, it is noted that in the embodiment 3 of FIGS. 1A, 1A' and 1B that the latching mechanism and elements arise predominantly from and deals solely with the adapter disc structures 4 and 5 and the oppositely positioned space-apart lateral projections 13a and 13b of adapter disc 5 and the oppositely positioned spaced-apart lateral projections 13aa and 13aa' of adapter disc 4, securable together by the two separate resilient annular members such as elastic bands 6a and 6b in accord with the illustrations. In contrast thereto, the latching mechanism and elements thereof of the embodiment 3' of FIGS. 2A, 2A' and 2B include the additional spaced-apart support-disc structures as annular plates 18 and 19 that each have a wider outside diameters and that carry the oppositely-positioned and spaced-apart latching lateral projections 13'a and 13'b on support-disc structure 18 and the 13'aa and 13'bb on support-disc structure 19, latchable or latched together as illustrated by resilient annular members such as elastic bands 6'a and 6'b.

Figures 2A, 2B:
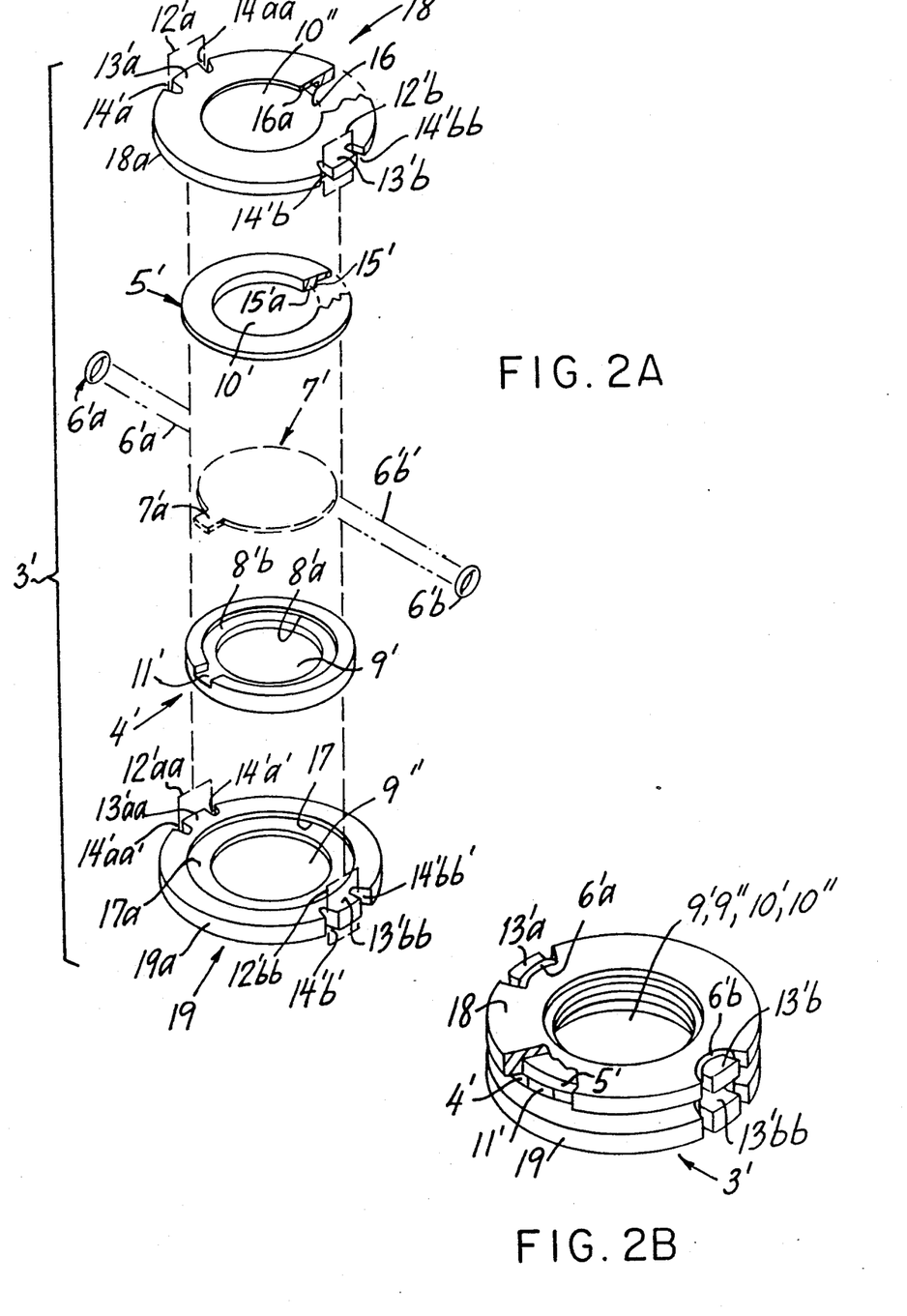
FIG. 2B likewise diagrammatically illustrates the FIG. 2A alternate preferred embodiment and features thereof, except here shown in non-exploded view as it would normally appear, except devoid of a transdermal patch mounted therein.
Figure 2C:
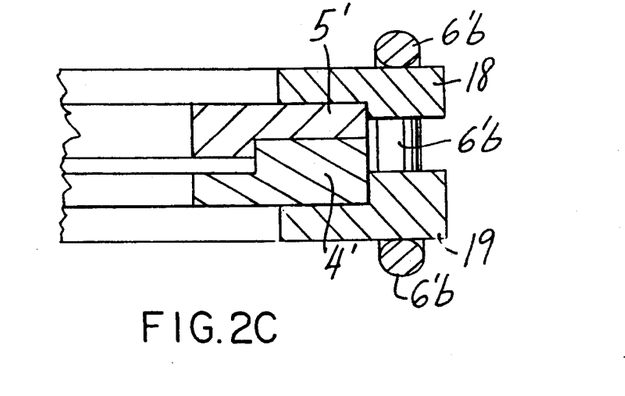
FIG. 2C diagrammatically illustrates an in part view in cross-section of the embodiment of FIG. 2B, devoid of transdermal patch therein.

Thus, FIGS. 1A, 1B and 1A' each diagrammatically illustrate the same preferred embodiment 3 of the invention, and FIGS. 2A, 2B and 2B' each diagrammatically illustrate an alternate preferred embodiment 3' of the invention.

In the exploded view of FIG. 1A embodiment 3, there is provided the adapter lower disc structure 4 commonly referred to as the lower adapter disc, and the adapter upper disc structure 5 commonly referred to as the upper adapter disc. Illustrated in phantom is the symbolic shape of a transdermal patch 7 shown in operative alignment between the lower disc structure 4 and the upper disc structure 5, positioned such that the transdermal patch's handle-tab 7a is aligned to be seated in the radially-outwardly and laterally-extending transdermal patch-seating cut-out and recess 11 thereof. This handle-seating or tab-seating recess 11 further anchors the transdermal patch 7, keeping the transdermal patch from being tilted as the main body of the patch 7 is seated within the disc stepped recess 8b formed between the downwardly-stepped wall 8a and the circular through-space 9. The tab-seating recess 11 communicates with the space of the stepped recess 8b and exterior space radially outwardly from the disc structure 4. The stepped recess 8b by seating the correspondingly-shaped transdermal patch 7, serves to prevent the transdermal patch 7 when so-seated from shifting and/or sliding to one or the other side before and/or during testing thereof, as well as facilitating easy and quick seating and exact alignment in order to assure repeatable and accurate test results thereon.

The upper disc structure 5 corresponds typically in its inner and outer diameter to the annulus structure thereof, and has the preferred downwardly-projecting stepped projection 15 that has at-least a minor degree less outer diameter as contrasted to the diameter of the stepped walls 8a of disc structure 4, in order that the projection 15 may be at-least partially pressed into the recess 8b as the projection 15 presses downwardly on top of the transdermal disc 7 to compress and thereby pin-down outer circumscribing top surfaces of the transdermal patch 7, to hold circumscribing portions of the transdermal patch 7 firmly and securely within the recess 8b. In this preferred embodiment 3, the upper disc structure 5 has a corresponding inner space 10 here corresponding in its annular-space shape's through-space 10 with the space 9 of disc structure 4. It is to be noted that most if not all transdermal patches have only one side thereof leachable, namely the side that in its intended use on the skin will face the skin for leaching drug or medication onto and/or into the skin. Accordingly, while it is necessary and essential and critical solely that at-least one of the upper disc structure 5 or the lower disc structure 4 have the through space(s) 10 or 9 respectively, in this preferred embodiment 3 both the adapter upper and lower disc structures have the through spaces 9 and 10 as illustrated, allowing the transdermal patch 7 to be seated either right-side-up or upside down devoid of any significant difference in leaching results, even though preferably the patch should be consistently placed therein in the same position for a series of repetitive and/or comparative tests. It should be also noted and recognized that apart from the mere arbitrary arrangement for purposes of illustration, the adapter upper and lower disc structures (plates) 4 and 5 may be oppositely arranged, i.e. the disc structure (plate) 4 as the upper disc structure (plate) and the lower disc structure (plate) 5 as the lower disc structure, although the arrangement illustrated is optimal for easy seating of the transdermal patch firmly within the recess 8b for easy and quick mounting of the transdermal patch 7.

In this particular embodiment 3, the latching mechanism and elements thereof include the respective circumscribing outer edge 4a of lower disc structure 4 and outer circumscribing outer edge 5a of upper disc structure 5, and in each of the upper and lower outer edges 4a and 5a have their respective oppositely-positioned and spaced apart (i.e. at opposite sides of the annular discs) lateral projections 13a and 13b (of disc structure 5) and 13aa and 13bb (of disc structure 4). In this preferred embodiment 3, the lateral projections above-noted are recessed such that the outer radially outwardly positioned ends of the lateral projections have outer diameters (across the annular disc structures 4 and 5) no greater than the outer diameter of these disc structures 4 and 5. This is accomplished in the illustrated preferred embodiment 3, by virtue of cut-out portions 14a and 14aa and 14b and 14bb of disc structure 5 and cut-out portions 14a' and 14aa' and 14b' and 14bb' of disc structure 4. Securable around the paired lateral projections 13a and 13aa is resilient annular member 6a (such as an elastic band), and securable around the paired lateral projections 13b and 13bb is resilient annular member 6b (such as another elastic band), as is shown in the non-exploded view of FIG. 1B—such as symbolically shown to assist understanding in FIG. 1A by the paired phantom brackets 12a, 12aa, and 12b, 12bb, together with the symbolic positioning phantom lines 6a' and 6b' for the annular resilient members 6a and 6b. It is noted that the FIG. 1B does not include illustration of the phantom-drawn transdermal patch 7 of FIG. 1A.

FIG. 1A' is a diagrammatic side view of the embodiment of FIGS. 1A, again illustrates the alignment of the various elements of preferred embodiment 3, together with disclosing parameter and/or dimension lines for thickness and/or inner and/or outer diameters, and relative seating alignment and size of the phantom-lined transdermal patch 7. More particularly, the cross-sectional area of the through-space(s) 9 and/or 10 has a preferred broad range of from about 0.125 inches to about 1.75 inches, and a more preferred diameter of from about 0.75 inch to about 1.5 inches, noting that this cross-sectional diameter is determined by and the same as either the inside diameter 25 of the recess-forming structure of recess 8b (and space thereof) for the adapter disc structure 4 and by the same as the inside diameter of the downwardly-extending projection 15 of the illustrated adapter disc structure 5, or alternately is formed by the inside diameter 25 of the downwardly-directed illustrated downward projection 15. The preferred broad-range diameter 21 of the first stepped indentation (as shown by indentation-phantom line 27b for the support structure thereof upon which a transdermal patch's outer surface would be seated) ranges from about 0.1 inch to about 2.25 inches, and from a more preferred narrow-range diameter of from about 0.85 inch to about 2.0 inches. However, as previously noted, the radially-extending width of the recess-support structure 27b defining (forming) the recess 8b has broadly sufficiently large size as to provide support for the seating thereof of a transdermal patch that extends across the through-space 10, preferably this support portion having a more preferred narrow range of from about 0.12 inch and 0.38 inch. Outside diameter(s) 22 of the upper and lower adapter disc structures 5 and 4 respectively, is only practically limited to inside diameter of tube(s) or vessel(s) to be utilized to seat the adapter disc structures within leaching liquid, but ranges preferably from about 1.7 inches to 2.6 inches. The outside diameter 24 of the downwardly-extending projection 15 is here illustrated as being less than the outer diameter 21 of the recess portion 27b. Except that the depth 27b of the recess 8b (and space thereof) be sufficiently deep to adequately support a transdermal disc to be seated therein and to be not too deep as to prevent the downwardly-extending projection 15 from being pressable downwardly on top of a transdermal patch to be seated in the recess 8b, recess depth may vary and likewise on the same basis the thickness(es) 20a and/or 20b of the adapter disc structure(s) 4 and 5 may vary. Likewise, the thickness of the downwardly-extending projection 15 may vary provided that it is sufficiently long (downwardly-extending) as to be pressable downwardly on top of a transdermal patch to be seated in the recess 8b.

In the preferred embodiment 3' of FIGS. 2A, 2B and 2A' and 2C, the latching mechanism and elements thereof include both an absence of any lateral projections on the disc structure 4 and/or 5, and a presence of additional upper and lower annular support-disc structures (plates) 18 and 19 as follows. The lower surface of the upper support-disc structure 18 has upward step-structure 16 forming recess 16a (and recess space thereof) for the seating and firm holding of the upper disc structure 5'. Accordindly, for this preferred embodiment having the seating recess 16a, the diameter of the annular step-structure 16 is at-least sufficiently larger than the outside diameter of the annular adapter disc structure 5' such that the adapter disc structure 5' is seatable within the recess 16a. Likewise, the lower support-disc structure 19 has downwardly-stepped structure 17 forming recess 17a (and space thereof) into which adapter disc structure 4' is seatable and securable against shifting, likewise the diameter of the annular downwardly-stepped structure 17 being at least sufficiently larger than the outer diameter of the adapter disc structure 4' such that the adapter disc structure 4' is seatable and securable within the recess 17 and space thereof. In this preferred embodiment 3', the support-disc plates 18 and 19 include the respective circumscribing outer edge 19a of lower support-disc structure 19 and outer circumscribing outer edge 18a of upper disc structure 19, and each of the upper and lower outer edges 18a and 19a have their respective oppositely-positioned and spaced apart (i.e. at opposite sides of the annular discs) lateral projections 13'a and 13'b (of support-disc structure 18) and 13'aa and 13'bb (of support-disc structure 19). In this preferred embodiment 3, the lateral projections above-noted are recessed such that the outer radially outwardly positioned ends of the lateral projections have outer diameters (across the annular support-disc structure 18 and 19) no greater than the outer diameter of these support-disc structure 18 and 19. This is accomplished in the illustrated preferred embodiment 3', by virtue of cut-out portions 14'a and 14'aa' and 14'b 14'bb' of support-disc structure 19 and cut-out portions 14'a and 14'aa and 14'b and 14'bb of disc structure 18. Securable around the paired lateral projections 13'a and 13'aa is resilient annular member 6'a (such as an elastic band), and Securable around the paired lateral projections 13'b and 13'bb is resilient annular member 6'b) such as another elastic band), as is shown in the non-exploded view of FIG. 2B—such as symbolically shown to assist understanding in FIG. 1A by the paired phantom brackets 12'a, 12'aa, and 12'b, 12'bb, together with the symbolic positioning phantom lines 6'a' and 6'b' for the annular resilient members 6'a and 6'b. It is noted that the FIG. 2B does not include illustration of the phantom-drawn transdermal patch 7' of FIG. 1A.

For an alternate preferred embodiment 3' of the FIGS. 2A, 2B, and 2A', the dimensions above-discussed for the adapter disc structure of the embodiment 3 equally apply to the embodiment 3'. Additionally, the support-disc structures 18 and 19 have recesses 16a and 17a of sufficiently large outside diameters 28 and 28' respectively to seat the respective adapter disc structures 5' and 4' as illustrated in the FIG. 2A', preferably these diameters being only slightly larger than the outer diameter 22' of the adapter disc structure 4'. Except that the depth 16a' and/or 16a" of the recess(es) 16a and/or 17a (and space thereof) be sufficiently deep to adequately support a transdermal disc to be seated on the support structure thereof, these recess depth(s) may vary and likewise on the same basis the thickness(es) 20'a and/or 20'b of the adapter disc structure(s) 4 and 5 may vary. Except for the provision as to being necessarily sufficiently thick and/or hard as to provide sturdiness and durability in the holding and supporting of the adapter disc structures 4' and 5', the thickness(s) 26a and 26b may vary as a mere matter of practicality, for the support-disc structures 18 and 19. Outside diameter(s) 22 of the upper and lower adapter disc structures 5 and 4 respectively, are only practically limited to inside diameter of tube(s) or vessel(s) to be utilized to seat the adapter disc structures within leaching liquid, but range preferably from about 1.7 inches to 2.6 inches.

As has been previously above set forth, in some preferred embodiments, the adapter disc structure(s) is/are made of polytetrafluoroethylene and/or of steel, and likewise for the support-disc structure(s). The commercially available steel well known in the industry most suitable for such steel preferred embodiments is commercially characterized as type 316 stainless steel.

A transdermal patch may have a drug reservoir (container/vessel in which the drug is leachably enclosed for leaching through a membrane) typically as small as 3 mm (millimeters) in diameter and typically as large as 25 mm. The size of the polytetrafluoroethylene (Teflon) and/or steel adapter disc structure(s) can vary or be varied to accomodate transdermal patch(es) and their drug-reservoir(s) of variable and/or different sizes and for a variety of variable and/or different shapes. Typical upper and/or lower adapter disc structure(s) have the step-formed recesses to locate and seat and secure the transdermal patch therebetween. A typical standard outer diameter of the assembly of the adapter disc structures of embodiments 3 and/or 4 has a 64 mm outer diameter and 33 mm inner diameter and thickness of 6 mm. The outer diameter of the assembly centers the patch in the round-bottom vessel for reproducible results by a leaching liquid such as water placed in the vessel. A primary benefit of the embodiments of the present invention, is that dead volume is minimized in the dissolution (leaching) vessel and leaching liquid thereof, also avoiding prior art requirements of adhesives and the like for anchoring transdermal patch(es). By the present invention, use thereof is easy and the assembly results in uniform and reliable testing conditions.

The present invention provides a versatile cell that aids in membrane development, and monitoring of membrane manufacturing. It can be used in the conventional dissolution apparatus to simulate release rates through membranes. A variety of test can be performed with the inventive embodiments and the container vessels thereof, such as finite and infinite testing on development membranes. Enhancer systems can also be tested with known membranes, and backings can be tested for impermeability. As with flux data, extrapolating data from these tests can give some correlation to in-vivo testing. The four-piece unit typically employs the polytetrafluoroethylene disc (Teflon), with several alternates having different sizes of recesses thereof for testing different sized transdermal patches. The above-described embodiment may be also utilized to secure tightly pressed, a cut-out membrane placed-over a drug reservoir of a transdermal patch, the mounted adapter disc assembly 3 or 3' or other embodiments there serving to seal the detached membrane to prevent leakage during the testing thereof. The embodiments of the invention are also convenient for quality control assessments of manufactured membranes and for stability monitoring of enhancer systems. It is also noted that for detached membranes to be tested, the recess spaces may be adapted to contain a drug and/or medication for a membrane to be anchored and tested by the latching elements previously described.

It is within the scope of the present invention to make such variations and modifications and substitution of equivalents as within the skill of the ordinary artisan in this particular field.

We claim:

1. A transdermal patch holder for making possible an ascertaining of release rate of drug carried by a transdermal patch during profiling of transdermal drug delivery systems, comprising in combination aligned separate upper and lower adapter disc structures each having opposite upper and lower surfaces, at least one of the upper and lower disc structures having a first through-space of predetermined first cross-sectional area extending between the upper and lower surfaces thereof, the lower surface of the upper disc structure having at-least some first outer portions thereof and the upper surface of the lower disc structure having at-least some second outer portions thereof with the first outer portions and the second outer portions in contact with one-another, at least one of the upper surface of the lower disc structure and the lower surface of the upper disc structure having a first stepped indentation of a first predetermined depth forming a first recess space in which outer edges of a transdermal patch having a second predetermined cross-sectional area greater than said first cross-sectional area are receivable and seatable, and latching means for intermittently latching-together said upper and lower adapter disc structures whereby a transdermal patch when seated within said first recess space is intermittently securely held in a supported state and position arranged for exposure to leaching liquid in contact with the transdermal patch through said first through-space by which drug is leachable from the transdermal patch, including substantially flattened through-channel structure constructed as part of said at-least one of the upper surface of the lower disc structure and the lower surface of the upper disc structure, the through-channel structure forming a through-channel space at at-least one of opposite sides of and in flow communication with said first recess space to sideward exterior space of which said through-channel structure is constructed and arranged to receive, mount and seat a radially-extending handle-tab of a transdermal patch when a transdermal patch is seated between the upper surface of the lower disc structure and the lower surface of the upper disc structure.

2. The transdermal patch holder of claim 1, in which each of said adapter disc structures has a substantially circular upright outer edge circumscribing and positioned between said upper and lower surfaces thereof and in which said first stepped indentation is of substantially circular shape.

3. The transdermal patch holder of claim 2, in which a remaining one of the lower surface of the upper disc structure and the upper surface of the lower disc structure has a stepped projection of increased disc structure-thickness of a predetermined thickness, said stepped projection having a substantially circular shape of a third predetermined cross-sectional area which is less in area than said second cross-sectional area such that said stepped projection is seatable within said first stepped indentation whereby said stepped projection is pressable on one surface of a transdermal patch sufficiently to restrain the transdermal patch when the transdermal patch is seated within said first stepped indentation.

4. The transdermal patch holder of claim 2, first through-space of predetermined major first cross-sectional area is of circular cross-section formed by an inside diameter of the first stepped indentation having an inside diameter ranging from about 0.125 inches to about 1.75 inches, and in which said first stepped indentation has an outside diameter ranging from about 0.1 inch to about 2.25 inches, wherein said inside diameter is selected to be smaller than said outside diameter, said first stepped indentation having a sufficiently small outside diameter as compared to an outside diameter of a drug reservoir such that a transdermal patch is supportable across said first through-space by support structure of the first stepped indentation.

5. The transdermal patch holder of claim 4, in which said inside diameter of the first stepped indentation ranges from about 0.75 inches to about 1.5 inches and in which said outside diameter of the first stepped indentation ranges from about 0.85 inches to about 2.0 inches, said first stepped indentation having support structure between said stepped indentation inside diameter and said stepped indentation outside diameter ranging from about 0.12 inch and 0.38 inch.

6. The transdermal patch holder of claim 5, in which said upper and lower adapter disc structures each have outside diameters ranging from about 1.7 inch to about 2.6 inch.

7. The transdermal patch holder of claim 6, in which said upper and lower adapter disc structures each have outside diameters ranging from about 1.0 inch to about 3 inches.

8. The transdermal patch holder of claim 6, in which each of said upper and lower adapter disc structures includes means defining said first through-space.

9. The transdermal patch holder of claim 8, said latching means including aligned upper and lower support-disc structures with the upper support-disc structure positioned above said upper adapter disc structure and with the lower support-disc structure positioned below said lower adapter disc structure, with the upper and lower adapter structures aligned with the upper and lower support-disc structures, each of the upper and lower support-disc structures having upper and lower faces, said upper and lower support-disc structures being intermittently securable with the upper support-disc having its lower face pressing downwardly on said upper surface of said upper adapter disc structure and with the lower support-disc having its upper face pressing upwardly on said lower surface of said lower adapter disc structure, at least one of said upper and lower support-disc structures having a centered through-space extending between said upper and lower faces.

10. The transdermal patch holder of claim 9, in which the lower face of the upper support-disc structure includes a second recess space of third predetermined cross-sectional area sufficiently large to receive and seat said upper disc structure, and in which the upper face of the lower support-disc structure includes a third recess space of fourth predetermined cross-sectional area sufficiently large to receive and seat said lower disc structure.

11. The transdermal patch holder of claim 10, in which each of said upper and lower support-disc structures includes said centered through-space.

12. The transdermal patch holder of claim 10, in which said latching means comprises at-least two opposite support-disc edges of each of said upper and lower support-disc structures, each of the opposite support disc edges including a lateral projection, and including at-least two elastic annular members each tightly mountable around each of aligned pairs of said lateral projections of the upper and lower support-disc structures whereby the upper and lower adapter disc structures are adapted to be intermittently held together.

13. The transdermal patch holder of claim 12, in which each said lateral projection is formed by spaced-apart cut-outs in said two opposite support-disc edges to define the lateral projection therebetween whereby distal portions of each lateral projection is substantially flush with its said upright outer edge.

14. A transdermal patch holder for making possible an ascertaining of release rate of drug carried by a transdermal patch during profiling of transdermal drug delivery systems, comprising in combination aligned separate upper and lower adapter disc structures each having opposite upper and lower surfaces, at least one of the upper and lower disc structures having a first through-space of predetermined first cross-sectional area extending between the upper and lower surfaces thereof, the lower surface of the upper disc structure having at-least some first outer portions thereof and the upper surface of the lower disc structure having at-least some second outer portions thereof with the first outer portions and the second outer portions in contact with one-another, at least one of the upper surface of the lower disc structure and the lower surface of the upper disc structure having a first stepped indentation of a first predetermined depth forming a first recess space in which outer edges of a transdermal patch having a second predetermined cross-sectional area greater than said first cross-sectional area are receivable and seatable, and latching means for intermittently latching-together said upper and lower adapter disc structures whereby a transdermal patch when seated within said first recess space is intermittently securely held in a supported state and position arranged for exposure to leaching liquid in contact with the transdermal patch through said first through-space by which drug is leachable from the transdermal patch, in which a remaining one of the lower surface of the upper disc structure and the upper surface of the lower disc structure has a stepped projection of increased disc structure-thickness of a predetermined thickness, said stepped projection having a substantially circular shape of a third predetermined cross-sectional area which is less in area than said second cross-sectional area such that said stepped projection is seatable within said first stepped indentation whereby said stepped projection is pressable on one surface of a transdermal patch sufficiently to restrain the transdermal patch when the transdermal patch is seated within said first stepped indentation.

15. The transdermal patch holder of claim 14, in which a remaining one of said aligned upper and lower adapter disc structures has a second through-space of predetermined major fourth cross-sectional area extending between the upper and lower surfaces thereof whereby each of opposite sides of a transdermal patch supported between the upper and lower aligned adapter disc structures is exposable to surrounding leaching liquid for the leaching of drug therefrom.

16. The transdermal patch holder of claim 15, in which said aligned upper and lower adapter disc structures are made of polytetrafluoroethylene.

17. The transdermal patch holder of claim 15, in which said aligned adapter disc structures are made of stainless steel.

18. The transdermal patch holder of claim 17, in which said upper and lower adapter disc structures each have a thickness ranging from about 0.045 inches to about 0.055 inches.

19. The transdermal patch holder of claim 17, in which said thickness ranges from about 0.025 inches to about 0.030 inches.

20. A transdermal patch holder for making possible an ascertaining of release rate of drug carried by a transdermal patch during profiling of transdermal drug delivery systems, comprising in combination aligned separate upper and lower adapter disc structures each having opposite upper and lower surfaces, at least one of the upper and lower disc structures having a first through-space of predetermined first cross-sectional area extending between the upper and lower surfaces thereof, the lower surface of the upper disc structure having at-least some first outer portions thereof and the upper surface of the lower disc structure having at-least some second outer portions thereof with the first outer portions and the second outer portions in contact with one-another, at least one of the upper surface of the lower disc structure and the lower surface of the upper disc structure having a first stepped indentation of a first predetermined depth forming a first recess space in which outer edges of a transdermal patch having a second predetermined cross-sectional area greater than said first cross-sectional area are receivable and seatable, and latching means for intermittently latching-together said upper and lower adapter disc structures whereby a transdermal patch when seated within said first recess space is intermittently securely held in a supported state and position arranged for exposure to leaching liquid in contact with the transdermal patch through said first through-space by which drug is leachable from the transdermal patch, said latching means comprising at-least two opposite edges of said upright outer edge of each of the aligned adapter disc structures, each of the opposite support edges including a lateral projection, and including at-least two elastic annular members each tightly mountable around aligned lateral projections of the upper and lower disc for each of the two opposite edges whereby the upper and lower adapter disc structures are intermittently held together.

21. The transdermal patch holder of claim 20, in which said lateral projection is formed by spaced-apart cut-outs in said upright outer edge defining the lateral projection therebetween whereby distal portions of each lateral projection are substantially flush with said upright outer edge.

22. A transdermal patch holder for making possible an ascertaining of release rate of drug carried by a transdermal patch during profiling of transdermal drug delivery systems, comprising in combination aligned separate upper and lower adapter disc structures each having opposite upper and lower surfaces, at least one of the upper and lower disc structures having a first through-space of predetermined first cross-sectional area extending between the upper and lower surfaces thereof, the lower surface of the upper disc structure having at-least some first outer portions thereof and the upper surface of the lower disc structure having at-least some second outer portions thereof with the first outer portions and the second outer portions in contact with one-another, at least one of the upper surface of the lower disc structure and the lower surface of the upper disc structure having a first stepped indentation of a first predetermined depth forming a first recess space in which outer edges of a transdermal patch having a second predetermined cross-sectional area greater than said first cross-sectional area are receivable and seatable, and latching means for intermittently latching-together said upper and lower adapter disc structures whereby a transdermal patch when seated within said first recess space is intermittently securely held in a supported state and position arranged for exposure to leaching liquid in contact with the transdermal patch through said first through-space by which drug is leachable from the transdermal patch, said latching means including aligned upper and lower support-disc structures with the upper support-disc structure positioned above said upper adapter disc structure and with the lower support-disc structure positioned below said lower adapter disc structure, with the upper and lower adapter structures aligned with the upper and lower support-disc structures, each of the upper and lower support-disc structures having upper and lower faces, said upper and lower support-disc structures being intermittently securable with the upper support-disc having its lower face pressing downwardly on said upper surface of said upper adapter disc structure and with the lower support-disc having its upper face pressing upwardly on said lower surface of said lower adapter disc structure.

23. The transdermal patch holder of claim 22, in which said upper and lower support-disc structures are stainless steel.

24. The transdermal patch holder of claim 22, in which the lower face of the upper support-disc structure includes a second recess space of third predetermined cross-sectional area sufficiently large to receive and seat said upper disc structure, and in which the upper face of the lower support-disc structure includes a third recess space of fourth cross-sectional area sufficiently large to receive and seat said lower disc structure.

25. The transdermal patch holder of claim 24, in which said latching means comprises at-least two opposite support-disc edges of each of said upper and lower support-disc structures includes a lateral projection, and including at-least two elastic annular members each tightly mountable around each of aligned pairs of said lateral projections of the upper and lower support-disc structures whereby the upper and lower adapter disc structures are adapted to be intermittently held together.

26. The transdermal patch holder of claim 25, in which each said lateral projection is formed by spaced-apart cut-outs in said two opposite support-disc edges to define the lateral projection therebetween whereby distal portions of each lateral projection is substantially flush with its said upright outer edge.

27. The transdermal patch holder of claim 26, in which said upper and lower support-disc structures each have outside diameters ranging from about 1.0 inch to about 3 inches.

28. The transdermal patch holder of claim 27, in which said upper and lower support-disc structures are stainless steel.

* * * * *